(12) United States Patent
Alford et al.

(10) Patent No.: US 6,355,225 B1
(45) Date of Patent: Mar. 12, 2002

(54) FULLERENE CONTRAST AGENT FOR MAGNETIC RESONANCE IMAGING AND SPECTROSCOPY

(75) Inventors: John M. Alford, Lakewood, CO (US); Lon J. Wilson, Houston, TX (US)

(73) Assignee: Wm. Marsh Rice University TDA Research, Inc., Houston, TX (US)

( * ) Notice: Subject to any disclaimer, the term of this patent is extended or adjusted under 35 U.S.C. 154(b) by 0 days.

(21) Appl. No.: 09/412,662

(22) Filed: Oct. 5, 1999

(51) Int. Cl.⁷ .................. A61B 5/055; G01N 24/00; A61K 51/00
(52) U.S. Cl. ............... 424/9.3; 424/9.32; 424/9.36; 436/173
(58) Field of Search ............... 424/9.3, 9.32, 424/9.36; 423/445 R, DIG. 39, DIG. 40; 436/173; 600/420

(56) References Cited

U.S. PATENT DOCUMENTS

| | | | |
|---|---|---|---|
| 4,478,816 A | 10/1984 | Ledley et al. .................. 424/4 |
| 4,647,447 A | 3/1987 | Gries et al. .................... 424/9 |
| 4,675,173 A | 6/1987 | Widder .......................... 424/9 |
| 4,770,183 A | 9/1988 | Groman et al. ............. 128/654 |
| 4,863,715 A | 9/1989 | Jacobsen et al. ............... 424/9 |
| 5,177,248 A | * 1/1993 | Chiang et al. ................. 560/86 |
| 5,248,498 A | * 9/1993 | Neumann et al. ............... 424/9 |
| 5,688,486 A | * 11/1997 | Watson et al. ............. 424/1.65 |
| 5,717,076 A | * 2/1998 | Yamamoto et al. ......... 534/558 |
| 5,994,410 A | * 11/1999 | Chiang et al. .............. 514/709 |

OTHER PUBLICATIONS

Tabata, Murakami and Ikada "Antitumor Effect of Poly (Ethylene Glycol)–Modified Fullerene", Fulerene Science and Technology, 5(5) 989–1007 (1997).

Krusic, Wasserman, Keizer, Morton, Preston "Radical Reactions of $C_{60}$", Science, 2554: 1183–1185 (1991).

Boulas, Kutner, Jones, and Kadish, "Bucky(basket)ball: Stabilization of Electrogenerated $C_{60}$ Radical Monoanion in Water by Means of Cyclodextrin Inclusion Chemistry", J. Phys. Chem. 1994, 98, 1282–1287.

* cited by examiner

*Primary Examiner*—Michael G. Hartley
(74) *Attorney, Agent, or Firm*—Conley, Rose & Tayon, P.C.

(57) ABSTRACT

A non-toxic contrast agent for enhancing contrast in in vivo magnetic resonance measurements, comprised of a water-soluble, stable paramagnetic fullerene that is free of paramagnetic metal species. A preferred contrast agent is a fullerol having at least one unpaired electron.

22 Claims, 3 Drawing Sheets

FULLERENE CONTRAST AGENT FOR MAGNETIC RESONANCE IMAGING AND SPECTROSCOPY

STATEMENT REGARDING FEDERALLY SPONSORED RESEARCH OR DEVELOPMENT

Research leading to this invention was federally supported, in part, by NIH grant number 1 R43 CA66363-01A1.

TECHNICAL FIELD OF THE INVENTION

This invention relates to compositions for improving magnetic resonance imaging ("MRI"), magnetic resonance spectroscopy ("MRS"), and magnetic resonance spectroscopy imaging ("MRSI") and more particularly to contrast agents that have particular affinity for certain tissues and can therefore be used as contrast agents. Still more particularly, the present invention relates to paramagnetic contrast agents that comprise stable fullerene molecules adapted to dissolve in aqueous solutions.

BACKGROUND OF THE INVENTION

Magnetic Resonance Imaging (hereinafter "MRI") is a powerful imaging tool that produces results analogous to x-ray images without requiring the application of harmful radiation. The nuclei of many atoms have a property called spin, which is associated with a small magnetic moment. In the absence of an external magnetic field, the distribution of the orientations of these magnetic moments is random. In the presence of a static external magnetic field, the nuclear magnetic moments precess about the field direction, producing a net alignment in the field. MRI works by exciting the molecules of a target object using a harmless pulse of radiofrequency ("RF") energy to excite molecules that have first been aligned using a strong external magnetic field and then measuring the molecules' rate of return to an equilibrium state within the magnetic field following termination of the RF pulse.

For example, in NMR imaging, a patient is placed in a static field and a short radio frequency pulse is applied via a coil surrounding the patient. The radio frequency or RF signal is selected for the specific nuclei (e.g. $^1H$) that are to be resonated. The RF pulse causes the magnetic moments of these nuclei to align with the new field and to precess in phase. On termination of the pulse, the moments return to the original distribution of alignments with respect to the static field and to a random distribution of precession phases, thereby giving off a nuclear magnetic resonance signal that can be picked up by a receiving coil. The NMR signal represents a proton density map of the tissue being studied.

Two additional values can be determined when the RF pulse is turned off and the nuclear magnetic moments are relaxing or returning to equilibrium orientations and phases. These are $T_1$ and $T_2$, the spin-lattice and spin-spin relaxation times. $T_1$ represents a time characteristic of the return to equilibrium spin distribution, i.e. equilibrium alignment of the nuclear magnetic moments in the static field. $T_2$, on the other hand, represents a time characteristic of the return to random precession phase distribution of the nuclear magnetic moments. Hence, the NMR signal that is generated may contain information on proton density, $T_1$ and $T_2$. The visually readable images that are generated as output are the result of complex computer data reconstruction on the basis of that information.

Because successful imaging depends on the ability of the computer to recognize and differentiate between different types of tissue, it is not uncommon to apply a contrast agent to the tissue prior to making the image. The contrast agent alters the response of the aligned protons to the RF signal. Good contrast agents interact differently with different types of tissue, with the result that the effect of the contrast agent is greater on certain body parts, thus making them easier to differentiate and image. Various contrast agents are known for various medical imaging techniques, including X-ray, magnetic resonance and ultrasound imaging. Magnetic resonance contrast agents generally function by modifying the density or the characteristic relaxation times $T_1$, $T_2$ and $T_2^*$ of the water protons, which results in resonance signals from which the images are generated.

A paramagnetic substance is one that contains one or more fundamental particles (i.e. electrons or protons) with a spin whose effect is not cancelled out by another particle with like spin. These particles create a small magnetic field that can interact with neighboring nuclear magnetic dipoles to cause a reorientation of the dipole, i.e. a change in nuclear spin and precession phase. Because of their ability to affect relaxation times, many paramagnetic substances have potential as contrast agents. Since the magnetic field created by an electron is much greater than that created by a proton, however, in practice only ions, molecular radicals or metal complexes or cluster complexes that are paramagnetic as a result of containing one or more unpaired electrons are used as paramagnetic MRI contrast agents.

The use of paramagnetic metal ions, such as Mn(II), as contrast agents in MRI was first proposed by Lauterbur et al. in 1978. Since that time, a wide range of paramagnetic metal ion chelate complexes have been proposed. Metal ions that are reasonably stable and possess the highest magnetic moment, such as $Mn^{2+}$, $Fe^{3+}$, and $Gd^{3+}$, are the most commonly employed, but any paramagnetic transition metal ion will also work. More recently the use of superparamagnetic particles as MRI contrast agents has been described in U.S. Pat. No. 4,863,715.

While metal ion contrast agents are often used in MRI, they are not suitable for all applications. For example, they are not particularly useful in certain body areas such as the gastrointestinal (GI) tract. In addition, these contrast agents can be toxic and chemically reactive in vivo. Hence, the majority of contrast agent research has focused on developing non-toxic, stable chelates for binding these metal ions. Attempts have been made to achieve tissue-specific MRI contrast enhancement, to decrease toxicity, or to enhance stability and/or relaxivity by coupling of the paramagnetic chelates, or metal complexing groups, to various macromolecules or biomolecules such as polysaccharides, proteins, antibodies or liposomes. Thus, for example, U.S. Pat. No. 4,647,447 discloses the use of salts of Gd(III) chelates of DTPA (diethylenetriamine pentaacetic acid). Current commercial products are based on Gd(III) chelates of DTPA, DOTA (1,4,7,10-tetraazacyclododecane -N, -N', -N", -N"', -tetraacetic acid), and other modifications or derivatives of these chelates. In addition to metal chelates, the use of these metal ions as colloidal oxides or sulfides and as small superparamagnetic clusters has also been investigated.

Nevertheless, each of these approaches still requires the placement in the body of elements that have a degree of toxicity. Because the body may not readily eliminate these toxic elements, there is a potential health risk associated with their use.

In the search for a highly effective, non-toxic contrast agent, fullerene molecules have received attention. Researchers have speculated that fullerenes might be used to safely encapsulate and carry medically useful metals to different parts of the body where they could then be used for diagnostic or therapeutic purposes. In this capacity, the fullerene would act as a carrier for a metal atom or ion and maintain the same functionality as the metal chelates described above. For example, U.S. Pat. No. 5,688,486 discloses using fullerene molecules as cages or carriers for diagnostic or therapeutic entities. In particular, molecules are disclosed that enclose or support metal atoms or ions, preferably those that are paramagnetic or a radioisotope or have a large x-ray cross-section. Most of the compounds disclosed in the '486 patent, however, still include undesirable and potentially toxic metals.

The '486 patent makes brief reference to paramagnetic compounds comprising carbon mesh. Regarding such compounds, the '486 patent states that, "In certain imaging modalities the macromolecular mesh may itself function as a contrast agent." The sole disclosure cited in the '486 patent that provides any disclosure of specific paramagnetic fullerene compounds that do not contain a metal ion is Krusic et al., Science, 254:1183–1185 (1991). Krusic teaches that benzyl and methyl radical R groups can be attached to fullerenes. Krusic does not teach that the resulting radical fullerene compounds have any use as contrast agents. Indeed, because the compounds disclosed by Krusic are not soluble in water and are prepared only under anaerobic conditions, they are ineffective as in vivo contrast agents. To be effective as in vivo contrast agents, compounds must have a solubility in water of at least 3 mM.

In addition to the non-water-soluble benzyl- and methyl-fullerene radicals disclosed by Krusic, it is known that an unstable paramagnetic $C_{60}^{-1}$ can be generated. This radical anion, while paramagnetic and free of heavy metals, is readily oxidized to its diamagnetic $C_{60}$ state and is thus unstable in air and water, making it, too, unsuitable for use as an in vivo contrast agent. In addition, the $C_{60}^{-1}$ monoanion, like the non-radical $C_{60}$, is hydrophobic and thus insoluble in water. Boulas et al., J. Phys. Chem., 98, 1282–1287 (1993) disclose a method for increasing the water solubility of fullerene molecules and ions by forming inclusion complexes of fullerenes within cyclodextrin molecules. The solubility (ca. $10^{-4}$ M) is not increased sufficiently to make the complex a practical contrast agent, however, and the compounds still have little use as in vivo contrast agents because of the likely instability of the $C_{60}^{-1}$ monoanion/cyclodextrin complex in the body.

Hence there remains a need for contrast agents having improved properties, e.g. in terms of contrast enhancement, water-solubility, biodistribution, stability, opacity, relaxivity, and tolerability.

SUMMARY OF THE INVENTION

The present invention relates to a contrast agent that is water-soluble, stable, and highly effective, yet is not toxic. The present contrast agent comprises paramagnetic fullerene molecules that are solubilized with hydroxyl groups. These compounds derive their magnetic relaxation efficacy from unpaired electrons associated with the fullerene cage. They are inherently magnetic and do not require the presence of internal paramagnetic ions or external linkage to paramagnetic metal ion chelates or other type of magnetic functional groups to achieve their relaxation ability. Therefore, they are substantially different from previously known fullerene-derived MRI contrast agents and constitute the basis for a unique new class of relaxation compounds.

According to a preferred embodiment, fullerene compounds are hydroxylated to form water-soluble paramagnetic compounds that can be used as MR contrast agents. The fullerene-based contrast agents do not need to include the toxic metals of prior contrast agents.

BRIEF DESCRIPTION OF THE DRAWINGS

For an introduction to the detailed description of the preferred embodiments of the invention, reference will now be made to the accompanying Figures, wherein.

DETAILED DESCRIPTION OF THE INVENTION

Figure 1:
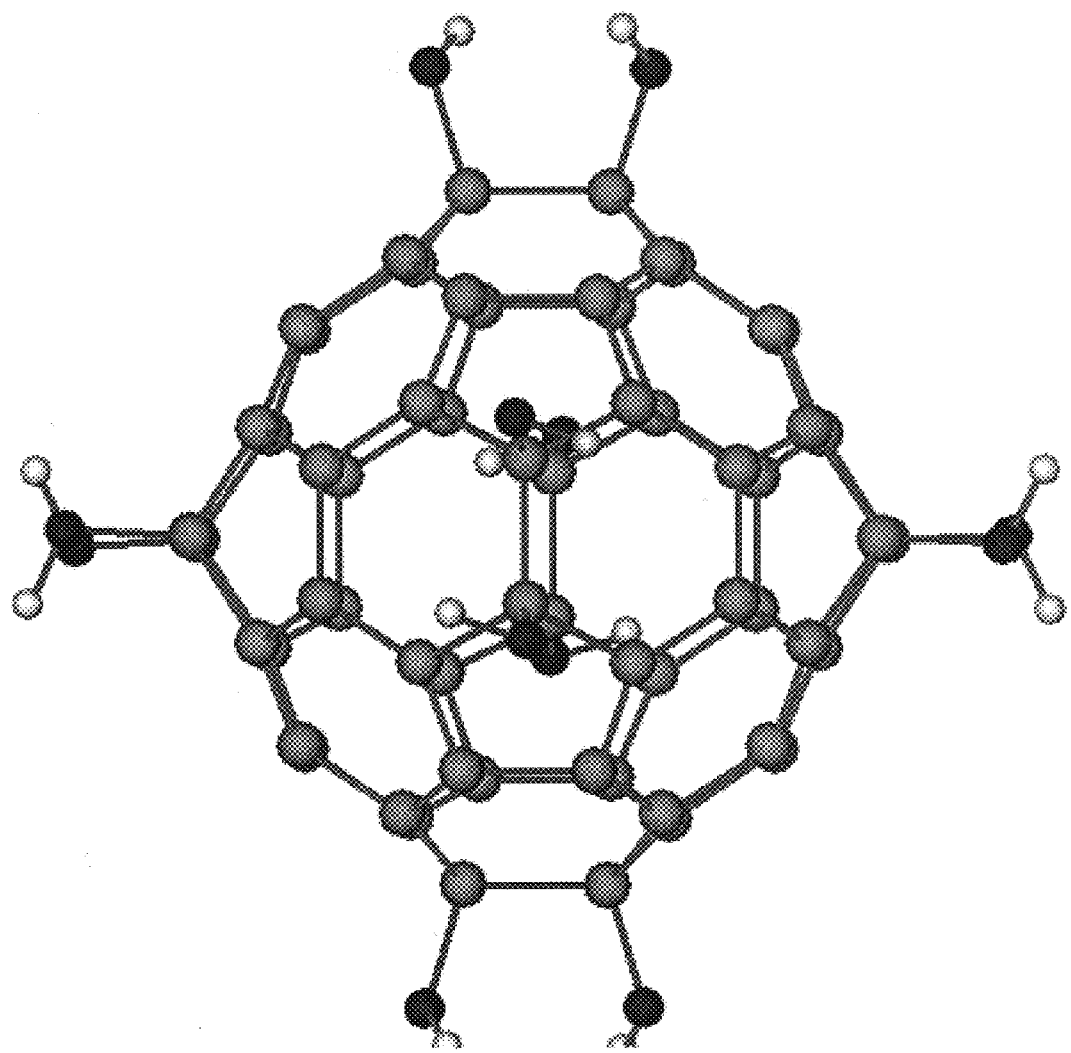
FIG. 1 is a proposed hypothetical structure for a first embodiment of a fullerene-based contrast agent according to the present invention.

It has been discovered that, in certain instances, the fullerene compound itself can be used as the active paramagnetic center to relax nearby excited magnetic nuclei. Fullerenes are sometimes referred to as "superatoms," and in this regard, the arrangement of molecular orbitals on the fullerene can be considered analogous to the atomic orbitals on an atom. If unpaired electrons are associated with the fullerene molecular orbitals, they will create a paramagnetic environment in the same manner as the unpaired d-electrons in $Fe^{3+}$ or the unpaired f-electrons in $Gd^{3+}$. This paramagnetism can then be utilized to relax the spins of nearby excited magnetic nuclei. Hence, the present invention provides fullerenes that include as part of their molecular structure stable molecular radicals or radical ions. In addition, the present fullerene molecules are sufficiently water-soluble for MRI contrast agent use as a result of the attachment thereto of multiple polar hydroxyl groups.

The physical phenomena involved in relaxing spins located near paramagnetic ions have been studied theoretically by Solomon, Bloembergen, and Morgan, and this analysis has allowed some of the more important features of a good relaxation agent to be understood. These features include: the number of unpaired electrons, the number of coordinated waters, the distance to the coordinated water(s), the exchange rate of the water(s), the excited electronic state lifetime of the unpaired electrons, and the rotational constant of the ion or ion chelate compound. These factors can then be used to aid in the design of new contrast agents.

One of the most important features of a contrast agent is the ability of the paramagnetic electron(s) to interact with the excited water protons. This includes the distance from the water to the paramagnetic electron and the rate at which the coordinated waters exchange. Because the magnetic dipole interaction falls off as $r^{-6}$, it is crucial to minimize this distance. Also, to relax as many protons as possible, the water exchange rate should be as close as possible to the inherent relaxation rate determined by the electronic and/or rotational correlation times. Permanently or slowly exchanging coordinated waters block access to the ion and do not contribute to the bulk water relaxivity. Therefore, the prior art chelates are designed to allow rapid exchange of water. For example, $Gd^{3+}$ has nine coordination sites and the $DPTA^{5-}$ chelate is designed to coordinate to eight of these sites, leaving one site for water coordination. Water coordinates to this site at a distance of 2.49 Å and exchanges at a rate of $4.1 \times 10^6$ sec$^{-1}$. Direct ion coordination sites are referred to as inner sphere and offer the highest relaxivity. The next water layer, which is blocked by the chelate or other permanently coordinated ligands, is referred to as the outer sphere. Its relaxivity is much lower due to the sharp drop-off of the dipole interaction with distance.

With respect to the importance of water access as described above, the $C_{60}(OH)_{12}^{1-}$ paramagnetic fullerene anion (FIG. 1) is an acceptable relaxation agent. In contrast to atomic orbitals, which are small and localized near the atomic nucleus, the highest energy molecular orbitals of the fullerene are conjugated pi-orbitals that are shared among most of the carbon atoms of the fullerene shell. Electrons in these orbitals are delocalized and free to "roam" about the surface of the fullerene as shown in FIG. 1, while electron population of other orbitals may be more or less delocalized. For perspective, a water molecule is also shown in FIG. 1. As can be seen, the surface area available for direct water access to the radical electron is very large ($\sim 200$ Å$^2$) and is easily an order of magnitude or more larger than the coordination site available to chelated metal ions. The present water-soluble fullerenes are not known to have permanent water coordination sites, and the exchange rate is predicted to be very rapid (limited by the rate water diffuses to the fullerene).

For the foregoing reasons, paramagnetic fullerenes have several of the attributes necessary to be good relaxation agents. By way of Example only, two embodiments of stable, paramagnetic fullerene contrast agents are described below.

According to one preferred embodiment, $C_{60}(OH)_{12}^{1-}$ is used as a contrast agent. A neutral fullerol of this composition has been synthesized (Chen et al. 1998), but its precise structure has not yet been determined. One possible tetrahedral structure for this water-soluble fullerene derivative is shown in FIG. 1. The twelve hydroxyl groups are located on what is referred to as the 6—6 equatorial or e bonds of the $C_{60}$ fullerene and provide the water solubility. It has been calculated (vida infra) that, as an anion, the $C_{60}(OH)_{12}^{1-}$ fullerene has an open shell electronic structure and is paramagnetic.

Figure 2:
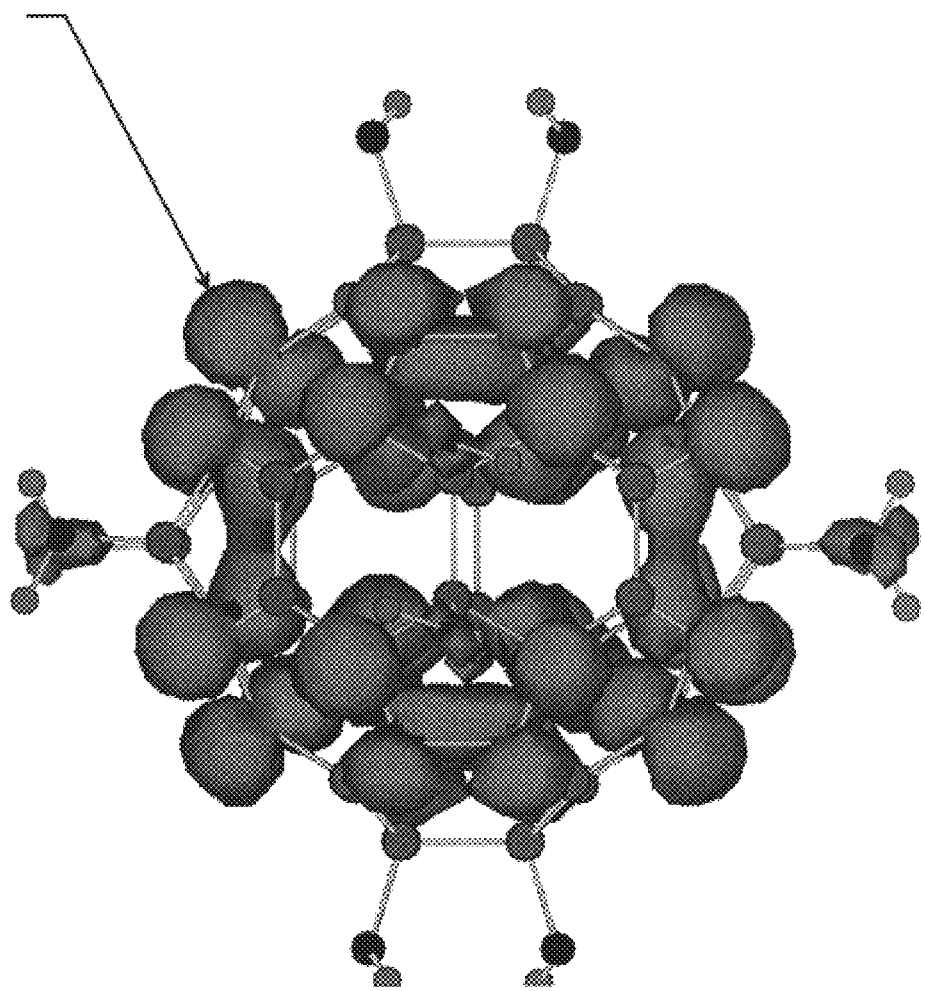
FIG. 2 shows a hypothetical distribution of the electron density in the highest occupied molecular orbital of the contrast agent shown in FIG. 1.

To gain more insight into the magnetic properties of $C_{60}(OH)_{12}^{1-}$, its electronic structure was analyzed using the semi-empirical quantum mechanical method MNDO-AM1. These calculations show that the unpaired or radical electron that provides the fullerene with the paramagnetism necessary to function as a relaxation agent is located in the highest occupied molecular orbital (HOMO). The electron density of the HOMO, derived from $\psi^2$ (the square of the wavefunction) and plotted at a contour value of $5 \times 10^{-4}$, is shown in FIG. 2. As is readily seen, this unpaired electron is delocalized over the surface of the fullerene shell. Hence, with respect to the importance of water access as described above, the $C_{60}(OH)_{12}^{1-}$ paramagnetic fullerene is suitable for use as a relaxation agent.

According to a second embodiment, a water-soluble, paramagnetic fullerene derivative comprising about 32 hydroxyl groups attached to $C_{60}$ fullerene was synthesized and shown to be air-stable, paramagnetic, and an efficient water proton relaxation agent.

The $C_{60}(OH)_{32}$ was synthesized using the method of Li et al., (1993). A solution of $C_{60}$ in toluene was allowed to react with concentrated KOH in water using several drops of tetrabutylammonium hydroxide (40 wt. % in water) as a phase transfer catalyst. After separation of the $C_{60}$ from the toluene organic phase, the toluene was decanted, and the precipitate was allowed to react with the KOH solution for two to three days. The remaining water was removed under vacuum, and the sample was washed extensively with MeOH to remove the KOH. The fullerol solid was then redissolved in water. Substantial KOH remained in the sample and produced a highly basic solution. The remaining KOH was removed from the sample by exhaustive size exclusion chromatography using Sephadex G25 type gel. The purified sample eluted from the column in a band at pH 6.4, indicating that most of the excess KOH had been removed. This process was then repeated three times, with the final pH being about 5.5. The sample was finally taken to dryness under vacuum at room temperature and then dried to constant weight under vacuum at 80° C. over $P_2O_5$. A matrix assisted laser desorption ionization (MALDI) mass spectrometry analysis of the sample showed attachment of at least 30 OH groups. An elemental analysis indicated the composition to conform most closely to $C_{60}(OH)_{32}$ [Calculated for $C_{60}(OH)_{32}$: H, 2.55; C, 56.97; O, 40.48; Analysis found: H, 2.53; C, 56.54; O, 40.93%].

The $C_{60}(OH)_{32}$ fullerol was found to be very soluble in water (at least 4 mM). The conductivity of the purified acid fullerol sample was examined and found to have a conductivity corresponding to an ion concentration between a one to one and one to two electrolyte. However, in its acid form, dissociation may not be complete, leading to a low measured conductivity. Therefore, the $C_{60}(OH)_{32}$ fullerol may exist as either its 1$^-$ anion, 2$^-$ anion ($C_{60}(OH)_{32}^{1-}$ or $C_{60}(OH)_{32}^{2-}$), or a mixture of these two states (samples often contained K$^+$ cations also). In any case, the conductivity studies established the ionic nature of the fullerol and further tests were performed to characterize its magnetic properties.

The magnetic properties of the fullerol were characterized by several methods. An initial assay of the bulk magnetization using an Evan's balance indicated that the compound was paramagnetic with a magnetization approximately equal to one or two free electrons per fullerol. A solid sample was further studied using a Quantum Design MPMS-5S QUID magnetometer operating at 5 Tesla. The magnetic behavior of the solid was observed to approximately follow the Curie-Weiss law and was consistent with a paramagnetic material with S=½. After correction for the diamagnetic contribution of the sample (using data from $C_{60}$ for the fullerene carbons and Pascal's constants for the OH groups), the final value of the effective magnetic moment, $\mu_b$, of the $C_{60}(OH)_{32}$ is approximately 1.5 Bohr magnetons at 300 K. Given the large diamagnetic contribution, uncertainty in the diamagnetic correction factors, and assuming no spin orbit or other types of spin coupling, this is within the experimental error for predicting one free electron per fullerol molecule in the solid state. A measurement of the paramagnetism of the solution form of the acid fullerol was then conducted using the NMR method employing $D_2O$ as the solvent and t-butyl alcohol as the reference compound. Measurement of the chemical shift of the reference peaks indicated a paramagnetism of 2.1 Bohr magnetons at 300 K when in solution.

The magnetism studies show that $C_{60}(OH)_{32}$ (as its 1- or 2- anion) is indeed paramagnetic, with either a doublet (one unpaired e−) or triplet (two unpaired e−) electronic ground state. The current set of measurements suggest that in solution, it is most likely an anion, $C_{60}(OH)_{32}^{1-}$, that has one unpaired electrons on the fullerene shell in a doublet configuration. These experimental results make $C_{60}(OH)_{32}$ (or $C_{60}(OH)_{32}^-$ or $C_{60}(OH)_{32}^{2-}$) the first reported water-soluble, air-stable fullerene paramagnetic radical.

Figure 3:
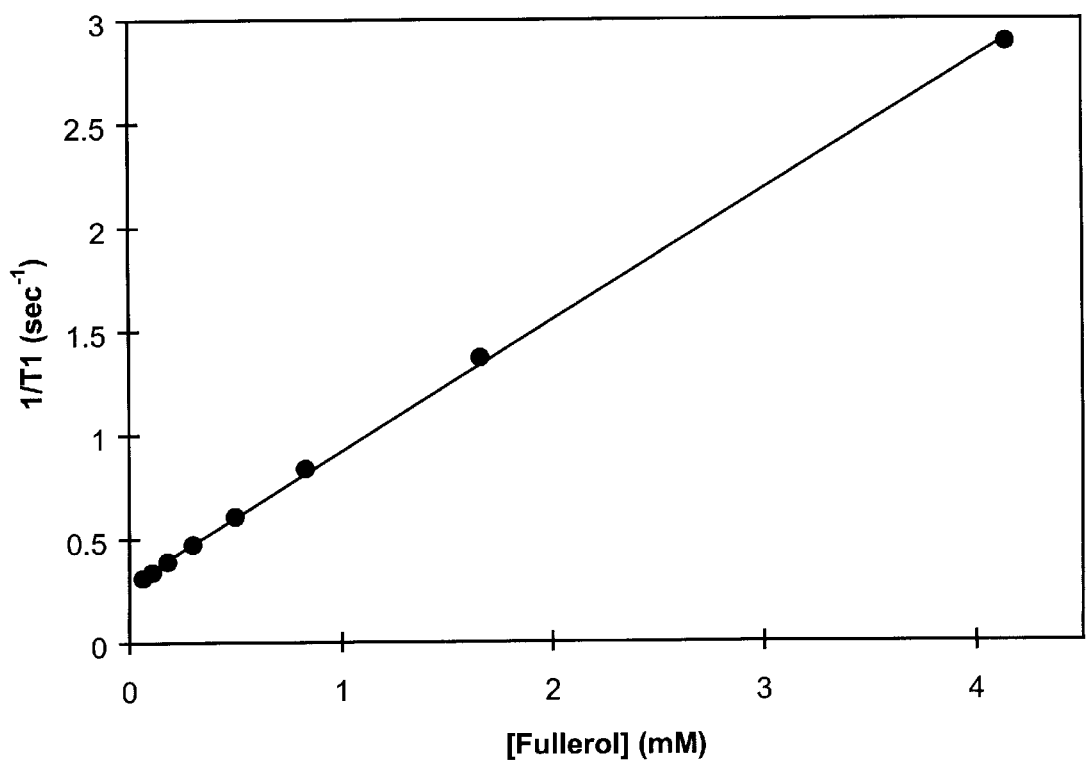
FIG. 3 is a plot of relaxivity vs. concentration for an alternative embodiment of a contrast agent according to the present invention.

The paramagnetic fullerol's potential as an MRI relaxation agent was evaluated by direct measurement of its water proton relaxivity using a Bruker model PC/20 relaxometer (Bruker Ltd., Canada) operating at a fixed field of 20 MHz (0.47 T) and 40° C. Four separate measurements at four different concentrations were performed to determine the $T_1$ relaxation. A plot of the results is shown in FIG. 3 and indicates a relaxivity of about 0.5 $mM^{-1}sec^-$. The relaxivity of the compound is thus considerably lower than the best currently available Gd-chelates (ca. 3.5 $mM^{-1}sec^{31\ 1}$) but is still large enough to be useful in the body.

Hence, the paramagnetic fullerols disclosed herein have utility as magnetic resonance imaging contrast or diagnostic agents. The water proton relaxation ability of paramagnetic fullerenes is shown to be useful, and recent biological studies indicate that fullerol and fullerene compounds in general are relatively nontoxic. Because they do not contain paramagnetic metal ions, there is no possibility of metal toxicity associated with these new fullerene compounds. This property makes them particularly attractive for applications where the imaging compound may be retained for long time periods or is otherwise subject to conditions where conventional metal chelates are unstable or metabolized. Furthermore, recent biological studies show that water-solubilized fullerols possess unique biodistributions and that they may be particularly useful as blood pool imaging agents for measuring blood flow and perfusion. By changing or adding functional group(s) on the fullerene cage, it should be possible to customize the biodistribution and preferentially carry the paramagnetic fullerene shell to any desired tissue in the body.

Other Embodiments

Because the active component of the present invention is the paramagnetic fullerene core, the present invention includes all magnetically relaxive fullerene compounds (including both neutral and ionic configurations) wherein the compound derives its primary relaxivity from a radical electron or electrons associated with the fullerene core, rather than from a paramagnetic metal ion. The present invention includes the use of these compounds as MRI relaxation agents. The present invention is not limited to $C_{60}$ fullerenes, as any size fullerene molecule or fullerene-related material, such as fullerene pipes, nanotubes, or nanoparticles (Liu et al. 1998; Chen et al. 1998) can be made paramagnetic according to the present invention.

There are many different ways to achieve a fullerene compound having a free-radical core. There also exist many methods for functionalizing the paramagnetic fullerene cage so that it can be safely employed in vivo for the MRI process. Methods that can be employed to produce a stable, water-soluble paramagnetic fullerene radical include, but are not limited to:

Chemical derivatization that produces a radical fullerene core as part of the reaction sequence. The sample reaction described earlier which uses sequential addition of $OH^-$ to produce the $C_{60}(OH)_{32}^{1-}$ anion is one such example.

Electrochemical oxidation or reduction. For example, a diamagnetic fullerene compound may be electrochemically reduced or oxidized to form a paramagnetic radical.

Chemical oxidation or reduction. For example, reduction of a diamagnetic fullerene compound may be accomplished with any sufficiently strong reducing or oxidizing agents to produce a paramagnetic radical.

The oxidizing or reducing agent may be incorporated within the fullerene. For example, any internally encapsulated metal such as alkali metals, alkaline earth metals, or lanthanide metals with a redox potential sufficient to reduce the fullerene cage and form a radical may be placed in the cage to form a paramagnetic complex such as $K^+@C_{60}(OH)_{32}^{1-}$.

The oxidizing or reducing agent may be linked to the fullerene shell. For example, a tertiary nitrogen group can be attached to the fullerene forming a charge transfer complex in which the radical electron is located on the fullerene shell.

The shell of the fullerene can be doped to achieve a radical electronic configuration. For example, a N atom may be incorporated into the fullerene shell to produce a radical such as such as $C_{59}N$.

The complex as a whole (the fullerene shell + its derivatives) may or may not be ionic, depending upon how the complex is designed. Some compounds, such as $C_{60}(OH)_{32}^{1-}$ are ionic, but other compounds may be built so that they are internally charge compensated such as $K^+@C_{60}(OH)_{32}^{1-}$ or other types of zwitterionic configurations. If the compound is ionic, then it can be administered with an appropriate biologically safe counterion such as glucamine$^+$, $Na^+$, $Cl^-$, or the like.

In order to operate effectively within a living body, the paramagnetic fullerene shell is preferably rendered water-soluble by an appropriate derivation process. This can be performed by derivatizing the fullerene shell with functional groups to impart water solubility and/or attaching the fullerene shell to a larger water-soluble molecule. The choice of functionalization method may be extremely important for obtaining the desired biodistribution, elimination pathways, or to reduce the toxicity of the compound. Some examples and potential uses of fullerenes in biology are given by Jenson et al. (1994). Several reactions for making fullerenes water soluble are described by Hirsch (1994) in his recent review of fullerene chemistry review Suitable method include but are not limited to:

Attachment of multiple hydroxy groups using the reaction of Li et al. as described above. Fullerenes can also be polyhydroxylated using the method described by Chiang et al. 1993.

Polyhydroxylated fullerenes can be further derivatized using the —OH groups to form new functional groups such as esters, for example.

Attachment of multiple carboxylic acid groups. This is conveniently performed using the Bingle-Hirsch reaction to add malonic acid groups to a fullerene (reviewed by Hirsch 1994). Other methods of adding carboxylic acid groups have been reported (Isaacs and Diederich 1993). The carboxylic acid provides a convenient method (through an amide linkage) to attach the $C_{60}$ to other water-solubilizing functional groups.

The fullerene cage can be attached to a polypeptide (Toniolo et al. 1994), oligonucleotide, monoclonal antibody or other types of amino acid sequences.

Addition of multiple amines (reviewed by Hirsch 1994) or amino acids (Zhou et al. 1995) can be used to solubilize the fullerene shell.

The addition of multiple alkyl sulfonates has been used to produce a water-soluble fullerene Chen et al. (1998).

The fullerene can be attached to water-soluble polymers such as PEG (polyethylene glycol), (Tabata et al. 1997). The paramagnetic fullerene can also be built into water-soluble dendrimers and the like. (reviewed by Hirsch 1994).

Furthermore, it is contemplated that other groups, including but not limited to alkyl and aliphatic groups, can be included on or in the present water-soluble fullerene radical without departing from the scope of the present invention.

What is claimed is:

1. A contrast agent for enhancing contrast in in vivo magnetic resonance measurements, comprising: a water-soluble, air-stable paramagnetic fullerene molecule, wherein the fullerene molecule has an unpaired electron.

2. The agent according to claim 1 wherein said fullerene is free of paramagnetic metal species.

3. The agent according to claim 1 wherein said fullerene has a solubility in water of at least 3 mM.

4. The agent according to claim 1 wherein said fullerene comprises a fullerol.

5. The agent according to claim 1 wherein said fullerene comprises a radical of $C_{60}(OH)_{12}$.

6. The agent according to claim 1 wherein said fullerene comprises a radical of $C_{60}(OH)_{32}$.

7. The agent according to claim 1 wherein the effective magnetic moment of said fullerene is at least approximately 1.5 Bohr magnetons at 300 K.

8. The agent according to claim 1 wherein the effective magnetic moment of said fullerene is at least approximately 2.0 Bohr magnetons at 300 K.

9. A method for making magnetic resonance measurements of a sample by modifying the characteristic relaxation times of water protons in the sample, comprising:

introducing a contrast agent comprising a water-soluble, air-stable paramagnetic fullerene molecule that includes an unpaired electron into the sample;

placing the sample in a magnetic field;

providing a radio frequency pulse to the sample; and measuring the relaxation times.

10. The method according to claim 9 wherein said fullerene is free of paramagnetic metal species.

11. The method according to claim 9 wherein said fullerene has a solubility in water of at least 3 mM.

12. The method according to claim 9 wherein said fullerene comprises a fullerol.

13. The method according to claim 9 wherein said fullerene comprises a radical of $C_{60}(OH)_{12}$.

14. The method according to claim 9 wherein said fullerene comprises a radical of $C_{60}(OH)_{32}$.

15. The method according to claim 9 wherein the effective magnetic moment of said fullerene is at least approximately 1.5 Bohr magnetons at 300 K.

16. The method according to claim 9 wherein the effective magnetic moment of said fullerene is at least approximately 2.0 Bohr magnetons at 300 K.

17. A method for enhancing contrast in magnetic resonance images of a sample of animal tissue, comprising: introducing a water-soluble, air-stable paramagnetic fullerene molecule into the sample and performing magnetic resonance imaging of the sample, wherein said fullerene molecule includes an unpaired electron.

18. The method according to claim 17 wherein said fullerene is free of paramagnetic metal species.

19. The method according to claim 17 wherein said fullerene has a solubility in water of at least 3 mM.

20. The method according to claim 17 wherein said fullerene comprises a fullerol.

21. The method according to claim 17 wherein said fullerene comprises a radical of $C_{60}(OH)_{12}$.

22. The method according to claim 17 wherein said fullerene comprises a radical of $C_{60}(OH)_{32}$.

* * * * *

UNITED STATES PATENT AND TRADEMARK OFFICE
CERTIFICATE OF CORRECTION

PATENT NO. : 6,355,225 B1
DATED : March 12, 2002
INVENTOR(S) : John M. Alford and Lon J. Wilson It is certified that error appears in the above-identified patent and that said Letters Patent is hereby corrected as shown below:

<u>Title page,</u>
Item [73], Assignee should read as follows:
-- [73] Assignee: Wm. Marsh Rice University
Houston, TX (US)
TDA Research, Inc.
Wheat Ridge, CO (US) --

Signed and Sealed this

Twenty-eighth Day of January, 2003

JAMES E. ROGAN
*Director of the United States Patent and Trademark Office*